(12) United States Patent
Wyss et al.

(10) Patent No.: US 6,936,250 B2
(45) Date of Patent: Aug. 30, 2005

(54) VACCINES ABSORBABLE BY THE TRANSMUCOSAL WAY

(75) Inventors: Rolando Wyss, Vaduz-Liechtenstein (CH); Bernad Bizzini, Albi (FR); Ivo Volpato, San Mariano (IT)

(73) Assignee: Grisotech S.A., Soazza (CH)

( * ) Notice: Subject to any disclaimer, the term of this patent is extended or adjusted under 35 U.S.C. 154(b) by 46 days.

(21) Appl. No.: 10/101,034

(22) Filed: Mar. 18, 2002

(65) Prior Publication Data

US 2003/0049279 A1 Mar. 13, 2003

(30) Foreign Application Priority Data

Mar. 19, 2001 (IT) ...................................... MI2001A0571

(51) Int. Cl.$^7$ ......................... A61K 39/00; A61K 39/02; A61K 39/38; A61K 39/385
(52) U.S. Cl. ............................. 424/184.1; 424/193.1; 424/197.11; 424/234.1
(58) Field of Search ........................... 424/184.1, 193.1, 424/197.11, 234.1

(56) References Cited

U.S. PATENT DOCUMENTS

| | | | |
|---|---|---|---|
| 4,470,967 | A | 9/1984 | Gough et al. |
| 5,900,238 | A | 5/1999 | Gombotz et al. |
| 6,048,536 | A | 4/2000 | Chatfield |

FOREIGN PATENT DOCUMENTS

| | | |
|---|---|---|
| CA | 2053829 | 4/1992 |
| EP | 0491125 | 6/1992 |
| WO | WO0050078 | 8/2000 |

OTHER PUBLICATIONS

Sorensen et al (Acta Pathologica Microbiologica et Immunologica Scandinavica vol. 92, No. 6, pp. 351–356, 1984).*
Plotkin et al (VACCINES, published by W.B. Saunders Company, Philadelphia, 1988, p. 571).*
McNeela EA, et al., "A mucosal vaccine against diphtheria: formulation of cross reacting material (CRM (197)) of diphtheria toxin with chitosan enhances local and systemic antibody and Th2 responses following nasal delivery", Vaccine, pp. 1188–1198 (2000).
Jabbal–Gill I., "Stimulation of mucosal and systemic antibody responses against *Bordetella pertussis* filamentous haemagglutin and recombinant pertussis toxin after nasal administration with chitosan in mice", Vaccine, pp. 2039–2046 (1998).
Illum, L., "Chitosan and its Use as a Pharmaceutical Excipient", Pharm. Res., pp. 1326–1331 (1998).
Bacon et al., "Carbohydrate biopolymers enhance antibody responses to mucosally delivered vaccine antigens", Infect. Immun., pp. 5764–5770 (2000).
Mi FL et al., "Porous chistosan microsphere for controlling the antigen release of Newcastle disease vaccine preparation of antigen–adsorbed microsphere and in vitro release" Biomaterials, pp. 1603–1612 (1999).
Seferian et al., "Immune stimulating activity of two new chitosan containing adjuvant formulations", Vaccine, pp. 661–668 (2000).
Baldrick, "Pharmaceutical excipient development: The Need for Preclinical Guidance", Regul. Toxicol. Pharmacol. pp. 210–218 (2000).
Calvo et al. "Chitosan and chitosan/ethylene oxide–propylene oxide block copolymer nanoparticles as novel carriers for proteins and vaccines", Pharm. Res. pp. 1431–1436 (1997).
Anderson, "Adjuvants and immunostimulants for enhancing vaccine potency in fish", Dev. Biol Stand, pp. 257–265 (1997).
Aizpurua et al., "Oral Vaccination . . . Indentification of Classes of Proteins that Provoke an Immune Response upon Oral Feeding", Journal of Exp. Medicine, pp. 440–451 (1998).
Pusztai et al., "Plant (Food) Lectins As Signal Molecules: Effects on the Morphology and Bacterial Ecology of the Small Intestine", Lectin Reviews, pp. 1–15 (1991).

\* cited by examiner

Primary Examiner—Mark Navarro
(74) Attorney, Agent, or Firm—Abelman, Frayne & Schwab

(57) ABSTRACT

The main object of the present invention is to provide polysaccharide-coated antigens derivatized with lectins for pharmaceutical use. In the vaccines, polysaccharides are preferably selected from the group consisting of chitosan, low-molecular-weight and high-deacetylation-degree chitosan, methyl glycol chitosan, alginic acid, polymannuronic acid and salts or derivatives thereof. In the vaccines of the invention, antigens are microorganisms, infectious agents or constituents thereof, hormones, enzymes, proenzymes, narcotics, bioactive peptides, metabolites, biological precursors, cell constituents, allergens, and the lectins are of vegetable origin.

16 Claims, No Drawings

VACCINES ABSORBABLE BY THE TRANSMUCOSAL WAY

FIELD OF THE INVENTION

The present invention relates to the production of vaccines against endogenous and exogenous antigens, derivatised with lectins, for oral and transmucosal administration to humans and animals.

PRIOR ART

As known, antigenic structures, used as active vaccines, may be absorbed by the nasal way when incorporated in chitosan.

Some works on the topic are worth being mentioned, i.e. those concerning the incorporation in chitosan of influenza virus antigens (U.S. Pat. No. 6,048,536), of diphtheric toxin antigens (E. A. McNeela, Vaccine 2000, 19:1188–1198), and of Bordetella pertussis antigens (I. Jabbal-Gill et al., Vaccine 1998, 16:2039–2046).

The method of antigen incorporation in chitosan is not always described in the aforementioned papers, but is often based on the antigen-chitosan chemical cross-linking.

It follows that the incorporation in chitosan of various molecules, among which the vaccines, finds a primary rationale in the possibility of mucous absorption, especially by the nasal way, and a second rationale in the fact that this polysaccharide, like others, exerts an immunostimulating action and, therefore, can enhance the antigen-induced antibody response (A. Bacon et al., Infect Immun. 2000, 68:5764–5770; D. P. Anderson, Dev. Biol. Stand. 1997, 90:257–265; P. G. Seferian et al., Vaccine 2000, 19:661–668). The preferred administration, known in the prior art, is by the nasal way.

It is also known that by binding lectin-type or lectin-similar molecules to antigenic substances (or active vaccines), it is possible to direct said substances towards mucous epithelial cells, which express gangliosides GM1 e GM2 (De Aizpurua et al., J. Exp. Med. 1988, 167:440–451), thus inducing their incorporation in and transport towards immunocompetent cells.

However, the use of lectins is limited by the untoward side effects produced by same, such as growth inhibition, reviewed by A. Pustzai et al. (in "Lectin Reviews", ed. Kilpatrick D. C. 1991, Vol. 1: pp. 1–15). It follows that the rationalisation of their use is highly desirable.

SUMMARY

It is the main object of the present invention to provide polysaccharide-coated antigens derivatised with lectins for pharmaceutical use. In said vaccines, polysaccharides are preferably selected from the group consisting of chitosan, low-molecular-weight and high-deacetylation-degree chitosan, methyl glycol chitosan, alginic acid, polymannuronic acid and salts or derivatives thereof. In the vaccines of the invention, antigens are microorganisms, infectious agents or constituents thereof, hormones, enzymes, proenzymes, narcotics, bioactive peptides, metabolites, biological precursors, cell constituents, allergens, and the lectins are of vegetable origin.

Also, this invention extends to the use of the claimed vaccines in the preparation of drugs for the prevention and treatment of growth-related disorders, and for the treatment of osteoporosis, ulcer, hypercholesteremia, obesity, infertility, lipoidosis, allergies.

The invention has for its object also the provision of a procedure for the preparation of said vaccines and of compositions containing, as active ingredient, polysaccharide-coated vaccines derivatised with lectins.

DETAILED DESCRIPTION OF THE INVENTION

The Applicants observed that when antigens, also of proteic nature, are coated with polysaccharides, they are absorbed by the mucosa and stimulate both local and humoral immunity. Furthermore, when antigens are conjugated or derivatised with lectins, they are more effectively directed towards the mucosal cells, in particular, those expressing gangliosides GM1 and GM2 (M cells) and which are involved in the stimulation of the local and systemic immune response. The incorporation in polysaccharides of antigens derivatised with lectins allows the exploitation of the directional effect of lectins that, being protected by the polysaccharide coating, do not produce concomitant undesired side effects. It follows that the exploitation of the lectin directional effect, of the polysaccharide protection and transport, and of the immunomodulating effect of some polysaccharides. e.g. chitosan, results in dosage control and elimination of side effects, if any, produced by lectins. The major advantage of the vaccines of the invention is that they are absorbed by the oral and by the transmucosal way. The vaccines according to the present invention are adsorbable either by direct local administration on external mucosae (nasal, pharingeal, rectal, vaginal, or intestinal mucosae) or by oral administration, the latter allowing the vaccines to reach the internal mucosae of the gastro-intestinal tract.

Furthermore, they are more efficacious than the corresponding coated- but non-conjugated vaccines, in that they are more efficiently directed towards the mucosal cells involved in the stimulation of the immune response.

It is, therefore, the main object of the present invention to provide polysaccharide-coated vaccines consisting of antigens derivatised with lectins, for pharmaceutical use.

According to the present invention polysaccharides form a protective coat surrounding the antigen-lectin conjugate and exert a triple action: they protect the antigen from the degradation due to proteolytic enzymes and gastric environment and, therefore, may be administered per os; isolate lectins from non-specific and potentially toxic absorption; and may have an immunostimulating effect. Therefore, polysaccharides carry the vaccines, while protecting their proteic structure and allowing their absorption by the oral and transmucosal ways in the active form.

The oral or transmucosal absorption has further advantages over the parenteral one. In the specific case of heterologous proteins, such as for example immunoglobulins, the oral or transmucosal absorption, which is slower and more gradual, allows better to control the immunoglobulins dosage and distribution in the blood, and does not alter their efficacy. The absorption by the oral and transmucosal ways of the vaccines according to the invention is slower and more gradual than that by the parenteral way: it follows that the conditions of antigen-immune system interaction may be better rationalised with time.

Derivatised antigens are incorporated in polysaccharides using polysaccharide preparations having different physico-chemical characteristics and different derivatisation degrees.

Polysaccharides are preferably selected out of chitosan, alginate and derivatives thereof, such as for example low-molecular-weight (150,000) chitosan, medium-molecular-weight (400,000) and high-deacetylation-degree chitosan, glycol chitosan, methyl glycol chitosan, Protasan™. Particularly preferred are methyl glycol chitosan, low-molecular-weight and high-deacetylation-degree chitosan, and polymannuronic acid (MW 5–10 kD), obtained e.g. by alginic acid enzymatic hydrolysis with the alginate-lyase enzyme, and derivatives thereof. Said polysaccharides or derivatives thereof are selected from the group capable of surrounding the structure to be incorporated (in the specific case, antigens derivatised with lectins), with a polymeric "thin layer" resistant to the enzymatic action and to the physicochemical variations of the digestive system. They are also capable of directing the incorporated structure towards mucous cells of the intestinal tract, thus facilitating their absorption and the immuno-stimulating properties.

Non-cross-linked polysaccharides are preferably used for immunoglobulins incorporation. Further advantages result from the absence of cross-linking: the process for the preparation of the complexes of the invention is simpler and the final product does not contain potentially toxic residues derived from chemical cross-linking.

A feature of the vaccines of the present invention is that the coat-forming polysaccharides and the antigens derivatised with lectins are not covalently bound. Said coat is something like a superficial envelope in the form of a gel, as is the case e.g. of alginic acid. The bonds between polysaccharides and derivatised antigens are not covalent, but are preferably non-specific, weak interactions or ionic bonds.

In the vaccines of the invention, antigens may be of an endogenous or exogenous origin. They are selected from the group consisting of: infectious agents or their constituents thereof, allergens or antigenic constituents or their epitopes thereof, hormones, enzymes and proenzymes, narcotics, bioactive peptides, metabolites, biological precursors, cell constituents.

According to a preferred feature of the invention, antigens of exogenous origin derive from infectious agents or are inactivated infectious agents. According to a preferred feature, said infectious agents are selected from the group of: Herpes simplex, cytomegalovirus (CMV), chicken pox virus, rubella virus, syncytial virus, respiratory virus, influenza virus, Epstein-Barr virus, chicken rhinotracheitis virus, chicken respiratory virus, *Listeria monocytogenes, Salmonella enteritidis, Salmonella typhi, Salmonella paratyphi, Salmonella typhimurium, Salmonella choleraensis, Clostridium tetani, Clostridium botulinum, Shigella flexneri, Candida albicans, Toxoplasma gondii* or antigenic components or soluble or insoluble fractions thereof. Particularly preferred are the vaccines consisting of candidin antigen extracted from *Candida albicans, Listeria* antigen, IRT (Infectious Rhinotracheitis) antigen and chicken respiratory virus antigen. According to the invention, said antigens are derivatised and/or inactivated by conjugation with lectins and incorporated in polysaccharides. According to a further preferred embodiment, exogenous substances are narcotics for which antibodies formation may be usefully induced, e.g. for the purpose of detoxification. According to this preferred embodiment, antigens are narcotics, particularly those selected from the group consisting of cocaine, heroin, lysergic acid (LSD) or salts or derivatives thereof, which are derivatised with lectins and incorporated in polysaccharides. Particularly preferred is cocaine.

A further and innovative application of the vaccines of the invention is the control of the subject physiological (endogenous) biofunctional equilibria. In fact, antibodies induction towards endogenous substances, such as peptides, hormones or cell constituents, results in a metabolic variation of the body functional state or even in the correction of some pathological conditions. By way of example, when the antigen is cholesterol, the production of specific antibodies induced by the vaccine of the invention allows a reduction in the circulating cholesterol level. According to this embodiment, it is possible to correct functional and metabolic disequilibria deriving from organic degenerations of different nature. Therefore, in this case, the vaccines of the invention preferably consist of glucagon, somatostatin, cholecystokinin, calcitonin and derivatives thereof and/or conjugates with lectins, in polysaccharides. The natural body homeostasis, maintained by all endogenous molecules and components, is implemented, at a physiological level, by natural antibodies and specific inhibitors. This equilibrium state is not impaired by the active vaccination with the vaccines of the present invention. Conversely, a vaccination of this type can restore the homeostasis in a number of pathological conditions, as for example those described in the present invention.

Particularly preferred are the vaccines in which the endogenous substance or endogenous cell component, hormone or bioactive peptide, is cholesterol or somatostatin, derivatised with lectins and incorporated in polysaccharides according to the invention.

In the vaccines according to the invention, lectins are chosen on the basis of their ability to direct vaccines towards mucosal cells, in particular M-cells, involved in the immune response.

Particularly preferred are the lectins exerting an agglutinating action and particularly those selected from the group consisting of proteins derived from: *Lens culinaris, Glycine max, Ulex Europaeus* (UEAI+UEAII), *Arachis hypogaea, Phaseolus vulgaris*. According to a preferred feature of the invention, lectins are chemically derivatised with the antigen according to methods known in the art and, preferably, are derivatised with the antigen in ratio of 1 antigen molecole to 1–10 lectin molecules. Alternatively, they may be directly mixed with the antigen by high-speed mechanical stirring at 4° C. to 20° C. for 1 min.

The applicants have surprisingly found that, when the vaccines of the invention are administered together with immuno-adjuvants derived from the lipid-free *Corynebacterium granulosum* fraction, and are incorporated in polysaccharides according to the procedure used for the incorporation of antigens derivatised with lectins, i.e. by mixing a concentrated solution of derivatised antigen or of a lipid-freed BVV fraction (0.5–50 mg/ml) in a suitable buffer, selected on the basis of criteria known in the prior art, heated from 25 to 65° C., with a polysaccharide-containing solution in a concentration of 0.1 to 10% by wt./vol. in a buffer having pH of 3.5 to 8.5, and by high-speed mechanical stirring for 30 sec to 2 min or occasionally for 3 to 5 times for 30 to 60 sec., the antibody response following the vaccine treatment is dramatically increased.

It is, therefore, a further object of the present invention to provide adjuvant complexes consisting of the lipid-freed *Corynebacterium granulosum* fraction (BVV), incorporated in polysaccharides selected in the group consisting of chitosan, alginate and derivatives thereof, such as for example, low-molecular-weight (150,000) chitosan, medium-molecular-weight (400,000) and high-deacetylation-degree chitosan, glycolchitosan, methylglycolchitosan, Protasan™.

Particularly preferred are methylglycolchitosan, low-molecular-weight and high-deacetylation-degree chitosan, and polymannuronic acid (MW 5–10 kD), obtained e.g. by enzymatic hydrolysis of alginic acid with alginate-lyase enzyme, and derivatives thereof. Said polysaccharides or derivatives thereof are selected from the group capable of forming, around the structure to be incorporated (in the specific case antigens derivatised with lectins), a polymeric "layer" resistant to the enzymatic activity and to the physicochemical variations of the digestive system. According to a therapeutic scheme, the administration of the vaccines of the invention consists in a primary vaccine dose for sensitisation, followed by booster doses, all administered by the oral way and/or transmucosal absorption. Alternatively, the oral or transmucosal administration of the vaccines of the invention is combined with a primary sensitisation dose administered by the parenteral way. In both cases, the oral or transmucosal dose consists of 1 to 50 mg/administration both in the primary sensitisation and booster doses. The number of sensitisation and booster administrations ranges from 3 to 10. According to the protocol, sensitisation by the parenteral way is effected with a single 0.5 to 5 mg dose.

According to a further embodiment of the invention, vaccines are administered by the oral and transmucosal ways. The phrase "transmucosal ways" refers to the buccal, perlingual, rectal, vaginal ways of administration.

According to a still further embodiment, the vaccines of the invention are used in the preparation of drugs for the treatment of narcotics overdose syndrome, for the prevention and treatment of growth-related disorders, osteoporosis, ulcer, hypercholesteremia, obesity, infertility and pregnancy and menopause-related syndromes, for increasing the physical resistance to stress, for the treatment of allergic disorders, coagulation diseases, as well as in the preparation of drugs for the prevention and treatment of bacterial, viral and mycotic infections.

The vaccines of the invention are for human and animal use and, being administered per os, are prepared in the form of additives to foodstuff and water. It follows that they may be administered more easily that the vaccines for parenteral use only. It is a further advantage of the invention that the claimed vaccines may be collected and/or concentrated by filtration; moreover, even when re-suspended in a physiological saline solution, such as PBS at 4° C., they remain active for a long time.

It is a further object of the present invention to provide compositions for oral administration containing, as the active ingredient, the vaccines of the invention combined with appropriate adjuvants and excipients, such as those used in the prior art for the preparation of granular foodstuff for humans and animals (cornstarch, etc.). Particularly preferred are the compositions containing, as active ingredient, the vaccines derivatised with lectins and incorporated in polysaccharides, combined with BVV immunostimulants complexes, i.e. consisting of the lipid-freed *Corynebacterium granulosum* fraction with suitable excipients and/or diluents.

It is a further object of the invention to provide a procedure for the preparation of the vaccines of the invention essentially consisting in the following steps: a) antigen derivatisation by formation of a covalent bond with lectins, in ratios of 1 antigen molecule to 1 to 10 lectin molecules, or a') preparation of the lipid-freed *Corynebacterium granulosum* fraction; b) incorporation of the derivatised (or conjugated) antigen obtained in step a) or of the lipid-freed *Corynebacterium granulosum* BVV fraction obtained in step a') in the selected polysaccharide, preferably alginic acid, chitosan or salts or derivatives thereof, with mechanical stirring at 25° C. to 65° C.

According to a preferred embodiment, the incorporation of derivatised antigens in polysaccharides (step b) is carried out by mixing a concentrated solution of antigen derivatised with lectins or of a lipid-freed BVV fraction (0.5–50 mg/ml) in a suitable buffer selected on the basis of criteria known in the prior art, heated to 25 to 65° C., with a polysaccharide-containing solution in a concentration of 0.1 to 10% by wt./vol. in a buffer having pH of 3.5 to 8.5, and with high-speed mechanical stirring for 30 sec to 2 min or occasionally for 3 to 5 times for 30 to 60 sec.

Experimental Part

EXAMPLE 1

Preparation of Antigens Derivatised with Lectins

Antigens of different nature were derivatised with commercially available lectins (e.g. from Sigma) according to the schemes indicated below. Lectins were chosen on the basis of their tropism.

1.a. *Salmonella Enteritidis* Antigen. *Salmonella Enteritidis* Derivatisation with Lectina *Lens Culinaris*

A pellet of *Salmonella enteritidis* bacteria was suspended in a 0.025 M NaIO4 solution in a 0.1 M acetate buffer, pH 5.5. The resulting suspension was stirred at room temperature for 20 to 60 min. "Oxidised" bacteria were collected by centrifugation, washed twice by centrifugation and suspended again in 0.1 M carbonate/bicarbonate buffer, pH 9.0. After the last washing (20 ml suspension), the bacteria suspended at O.D. (620 nm)=1, in carbonate buffer, were added under stirring with Lectina (Sigma L9267) (5 μg) dissolved in the buffer (1 ml) and caused to react at room temperature for 4 hrs. Once the reaction was completed, the bacteria were settled by centrifugation and suspended again in PBS at D.O. (620 nm)=1 to 4.

1.b. *Listeria Monocytogenes* Antigen. *Listeria Monocytogenes* Derivatisation with Lectina *Glicina Max* (Sigma L1395)

The method used was similar to that followed for *Salmonella enteritidis* bacteria derivatisation.

1.c. Calcitonin Antigen. Calcitonin Derivatisation with Lectina *Ulex Europeus* (UEAI+UEAII)

A KLH (Keyhole Lymphet Haemocyanin, Sigma H8283) solution (1 ml) in PBS (10 mg/ml) was activated by dialysis overnight against 0.2% glutaraldehyde (200 ml) in PBS. Excess glutaraldehyde was eliminated by two dialyses, 4 hrs each, against 0.1 M bicarbonate/carbonate buffer (200 ml), pH 9.5.

The activated KLH solution was added with a solution (5 ml) consisting of salmon calcitonin (Sigma T3660) (1.5 mg) and Lectina *Ulex Europeus* (UEAI+UEAII) (Sigma L6762) (7.5 mg) in 0.1 M carbonate buffer, pH 9.5, containing 30% DMSO. The mixture was stirred overnight at 4° C. The reaction was discontinued by addition of 2.5 M glycine (50 μl). The resulting mixture was allowed to stand at room temperature for 2 hrs and dialysed against PBS.

1.d. Glucagon Antigen. Glucagon Derivatisation with Lectina *Arachis Hypogea*

A KLH solution (1 ml) activated with glutaraldehyde, according to the scheme described for calcitonin derivatisation, in a concentration of 10 mg/ml in 0.1 M bicarbonate/carbonate buffer, pH 9.5, was added with an N/500 NaOH solution (5 ml) containing a mixture of glucagon (Sigma G1774) (13 mg) and Lectina *Arachis Ipogea* (1.5 mg). (Sigma L0081)

The reaction was carried out overnight with stirring at 4° C. and discontinued by addition of 2.5 M glycine (50 μl). The resulting mixture was allowed to stand at room temperature for 2 hrs and dialysed against PBS.

1.e. Somatostatin Antigen. Somatostatin Derivatisation with Lectina *Ulex Europeus* (UEAI+UEAII)

Somatostatin (Sigma S9129) (3 mg) was dissolved in 0.1 M PBS (1.5 ml) and added with a 25% glutaraldehyde solution (0.3 ml). The resulting solution was caused to react in the dark and with stirring at 24° C. for 3 hrs, allowed to stand for 3 hrs and added with a UEAI+UEAII (Sigma L6762) (20 mg) solution in PBS. The mixture was caused to react for 1 hr, added with a 2 M glycine solution (0.1 ml), and caused to react at 24° C. for 1 hr.

1.f. Cholecystokinin Antigen. Cholecystokinin Derivatisation with Lectina *Phaseolus Vulgaris*

A KLH solution (1 ml) activated with glutaraldehyde in a bicarbonate buffer, pH 9.5, as described for calcitonin derivatisation in step 1c., was added with a solution (5 ml) containing a mixture of cholecystokinin (Sigma P4429) (1.5 mg) and Lectina *Phaseolus vulgaris* (Sigma L2769) (5 mg) in a 0.1 M bicarbonate/carbonate buffer, pH 9.5, containing 25% DMSO. Once the mixture was stirred overnight at 4° C., the reaction was discontinued by addition of 2.5 M glycine (50 µl). The resulting mixture was caused to react at room temperature for 2 hrs and dialysed against PBS.

1.g. Cholesterol Antigen. Cholesterol Derivatisation with Lectina *Ulex Europeus* (UEAI+UEAII)

Cholesterol (1 mg) was dissolved in a 5% Na2SO4 solution (2 ml) containing 30% DMSO. 3.8 ml of a solution of KLH activated with glutaraldehyde . . . (10 mg/ml in PBS) were added with a 36% formaldehyde solution (1 ml) and a UEAI+UEAII solution (10 mg/ml in PBS).

The reaction was continued for 4 hrs at room temperature, then overnight at 4° C. The reaction mixture was added with 2.5 M glycine (50 µl) and, after 2 hrs, was dialysed against PBS.

1.h. Cocaine Antigen. Cocaine Derivatisation with Lectina *Ulex Europeus*

Cocaine (Sigma C5776) was prepared as described by O. Bagasra et al. (Immunopharmacology, 1992, 23:173). Cocaine (4 mg) was dissolved in a 0.1 M NalO4 aqueous solution. The solution was stirred at room temperature for 20 min, added dropwise with a 5 ml of a solution containing KLH (1 mg) and Lectina *Ulex Europeus* (5 mg), in a 0.1 M bicarbonate/carbonate buffer, pH 9.5, while the pH was adjusted at regular intervals. The solution was further stirred for 4 hrs.

After that time, the solution was added with NaBH4 (10 mg) dissolved in water (0.5 ml), allowed to stand overnight at 4° C. and dialysed against 0.001 M PBS, pH 7.4.

1.i. *Candida albicans* Antigen. Candidin from *Candida albicans* Derivatisation with Lectina *Lens culinaris*

Candidin (10 mg) was dissolved in PBS (5 ml) and activated overnight by dialysis against 0.2% glutaraldehyde (200 ml) in PBS. Excess glutaraldehyde in activated candidin was eliminated by two subsequent 4-hr dialyses against 0.1 M bicarbonate/carbonate buffer (200 ml), pH 9.5.

Activated candidin was added with Lectina *Lens culinaris* (10 mg), dissolved in the same buffer (5 ml). The reaction was carried out overnight at 4° C. and discontinued by addition of 2.0 M glycine (100 µl). The resulting mixture was caused to react at room temperature for 2 hrs.

Derivatised candidin was dialysed against PBS.

1l. Rhinotracheitis Virus Antigen. Derivatisation of the Vaccine Against Rhinotracheitis with Lectina *Ulex Europeus*

Lectina *Ulex Europeus* (5 mg) (L6762 SIGMA) dissolved in PBS (1 ml) was activated overnight by dialysis against 0.2% glutaraldehyde in PBS. Activated Lectina was dialysed against 2 changes of 0.1 M bicarbonate/carbonate buffer (200 ml), pH 9.5 (4 hrs each time).

Activated Lectina was added to the vaccine (10 ml) under gentle stirring and the reaction, carried out overnight with further stirring, was discontinued by addition of 2.0 M glycine (50 µl).

Alternatively, native Lectina was directly mixed with the vaccine before incorporation in chitosan or alginate.

1.m. Respiratory Virus Antigen. Derivatisation of the Vaccine Against the Respiratory Virus with Lectina *Ulex Europeus*

Derivatisation was carried out as described for the preparation of the vaccine against rhinotracheitis virus, commercially available.

Lectina was added to the vaccine by mixing before incorporation in chitosan and alginate.

1.n. *Poa Pratensis* Antigen. *Poa Pratensis* Allergen Derivatisation with Lectina *Lens Culinaris*

Powdered *Poa pratensis* allergen (Sigma P 8895) (10 mg) was resuspended in phosphate/saline buffer PBS (5 mL) and activated overnight by dialysis against 0.2% glutaraldehyde in PBS (200 mL).

Excess glutaraldehyde in the activated allergen was eliminated by two subsequent 4-hr dialyses against 0.1 M bicarbonate/carbonate buffer (200 mL), pH 9.5.

The activated allergen was added with Lectina *Lens culinaris* (Sigma L9267) (10 mg) dissolved in the same buffer (5 mL). The reaction was carried out overnight at 4° C. and discontinued by addition of 2.0 M glycine (100 µL). The resulting mixture was caused to react at room temperature for 2 hrs.

The derivatised allergen was dialysed against PBS.

EXAMPLE 2

Derivatised Antigens Incorporation in Polysaccharides

Antigens derivatised as described in Example 1 were incorporated in polysaccharides (chitosan and alginic acid).

2.a. Incorporation in Chitosan

For antigens incorporation, use was made of chitosan preparations having different characteristics, e.g. low-molecular-weight (150,000) chitosan, medium-molecular-weight (400,000) and high-deacetylation-degree chitosan, glycol chitosan, methyl glycol chitosan, Protasan™.

Chitosan (MW 750 kD, Fluka 22742) (0.2%–1%) was dissolved in a 0.025 M acetate buffer, pH 5.7. The derivatised antigens solution was dissolved in 0.05 M Na2SO4 (10 mg in 2.5 ml).

Each solution was heated to 55° C. on a water bath. The chitosan solution (2.5 ml) was added to the derivatised antigens solution (2.5 ml) and the mixture was vortexed at the max. speed for 20 to 60 sec.

2.b. Incorporation in Alginate

Antigen-lectin derivatives in PBS (10 mg in 50 ml) were added with one volume of low-viscosity sodium alginate (Fluka 71238) (1 to 5%) in PBS. The mixture was vortexed at the max. speed for 30 to 120 sec.

Note: All incorporated antigens prepared as described above may be collected by filtration and stored, in a refrigerator, in a small volume of PBS or physiological solution.

EXAMPLE 3

Preparation of Adjuvant BVV Complex in Polysaccharides 3.a. Preparation of the BVV Fraction from *Corynebacterium granulosum*

The BVV fraction, corresponding to the *Corynebacterium granulosum* particle fraction, was obtained from a microorganism culture. The culture was inactivated by heating to 60° C. for 30 min. The culture, cooled to room temperature, was centrifuged for bacteria collection. The bacterial mass was washed by resuspension in a physiological solution and by centrifugation. Washing was repeated once again and bacteria were delipidated by extraction with organic solvents and broken down by waring blendor. Unbroken bacteria were removed by a 10-min low-speed centrifugation. The surnatant was subjected to high-speed centrifugation (10.000 rpm, 30 min) to collect bacterial fragments. The sediment, mainly consisting of glycoproteins and peptidoglycans, represented a particle fraction denominated BVV.

3.b. Preparation of BVV Complex in Chitosan

An insoluble particle suspension from *Corynebacterium granulosum* (BVV) in a concentration of 200 to 2000 μg/ml in 50 mM Na2SO4, was heated to 55° C. on a water bath and added with the same volume of 0.2 to 4% chitosan solution in a 25 mM acetate buffer, pH 5.7. The mixture was heated to 55° C. and vortexed at the max. speed for 30 to 120 sec.

3.c. Preparation of BVV Complex in Alginate

One volume of BVV suspension in PBS (200 to 2000 μg/ml) was added with one volume of low-viscosity sodium alginate solution (1 to 5%) in PBS. The mixture was vortexed at the max. speed for 30 to 120 sec.

The BVV fraction administered with vaccines exerted an immunostimulating action consisting in the enhancement of the vaccine-induced antibody response. Administration was carried out by combining, in appropriate ratios, the incorporated BVV fraction with vaccine.

EXAMPLE 4

Immunisation with the Vaccines of the Invention and Analysis of the Vaccine Efficacy (Antibody Production In Vivo)

Animals were treated with the vaccines of the invention consisting of the antigen derivatised with lectin and incorporated in the aforementioned polysaccharides.

4.a. Evaluation of the Antibody Response to the Vaccination Against Polysaccharide-Complexed *Salmonella Enteritidis* Antigen in the Rabbit The vaccine consisting of *Salmonella* antigen conjugated with lectin and incorporated in chitosan or alginate was mixed with the feedstuff and pelletized. Rabbits were administered the vaccine according to the experimental scheme (A):

1. on day zero and on the next three days, administration of 1 mg/kg/die of derivatised and incorporated *Salmonella* antigen partitioned in the daily diet;
2. on day 21, administration of 0.5 mg/kg of *Salmonella* antigen partitioned in the daily diet;

or alternatively according to the experimental scheme (B):

1. on day zero, rabbits were injected a single dose of vaccine subcutaneously, corresponding to 1 mg/kg of *Salmonella* antigen; (sensitization step);
2. on day 7 rabbits were administered a dose of vaccine corresponding to 0.5 mg/kg of *Salmonella* antigen, mixed with the daily diet;
3. on days 14 and 21 rabbits were administered a booster mixed with food at the same dose and according to the same procedure as described above.

Twenty animals were used for each experimental scheme. Sensitisation (Step treatment No. 1 according to scheme B) was performed on the 30th day of life.

For the evaluation of the antibody response, 15 days from the last booster dose, a blood sample was taken from the ear marginal vein of the animals.

Antibody production was evaluated by the immunoenzymatic (ELISA) test with *Salmonella* antigen (solubilised fraction) adhering to the microplate well and by detecting immunoglobulins bound by addition of a rabbit anti-immunoglobulin antibody conjugated with peroxidase, followed by addition of a specific chromogen for the enzyme.

The colour intensity was directly proportional to the amount of specific anti-*salmonella* IgGs contained in the antiserum.

By way of comparison, a group of animals was treated, according to the same procedure and dosages, with antigen non-derivatised with lectins, but incorporated in chitosan.

Table 1 shows the mean O.D. values at different serum dilutions obtained according to the two experimental vaccination schemes.

TABLE 1

Specific antibodies dosage following vaccination with salmonella antigen

| Group | Treatment | Mean O.D. at different serum dilutions 1:5000 | 1:20000 | 1:80000 |
|---|---|---|---|---|
| A | Blank | 0.030 | | |
| B | Controls: no vaccination | 0.450 | 0.320 | 0.140 |
| C | Treated with vaccine in chitosan Experimental scheme (A) | 2.240 | 1.850 | 1.175 |
| D | Treated with vaccine in chitosan Experimental scheme (B) | 2.400 | 2.040 | 1.820 |
| E | Treated with vaccine in alginate Experimental scheme (A) | 2.300 | 2.210 | 1.940 |
| F | Treated with vaccine in alginate Experimental scheme (B) | 2.080 | 1.860 | 1.740 |
| G | Treated with non-derivatised vaccine, incorporated in chitosan Experimental scheme (A) | 1.420 | 0.870 | 0.560 |

The data reported in Table 1 show that the vaccines prepared as per Example 1 (derivatised with lectins and incorporated in chitosan) induce antibodies production according to experimental immunisation protocol A as well as to experimental immunisation protocol B. The table also shows that the vaccine non-derivatised with lectin, but incorporated in chitosan, is less efficacious than the vaccine derivatised with lectin.

4.b. Evaluation of the Antibody Response to the Vaccination Against Polysaccharide-Complexed *Listeria Monocytogenes* Antigen in the Rabbit The vaccine consisting of *Listeria* antigen conjugated with lectin and incorporated in chitosan or alginate was tested for the antibody response in the rabbit. Rabbits were administered the vaccine, by the oral way, mixed with the foodstuff, according to the following two physiological schemes:

Scheme A:

1. on day zero and on the next three days, administration of vaccine mixed with the foodstuff at a dose corresponding to 1 mg/kg/die of *Listeria* antigen;
2. on days 21 and 22, administration, according to the same procedure, of a dose corresponding to 0.5 mg/kg/die of *Listeria* antigen partitioned in the daily diet.

Scheme B:
1. on day zero, subcutaneous injection of a quantity of vaccine corresponding to 1 mg/kg of *Listeria* antigen (sensitisation step);
2. on days 1, 14 and 21, administration by the oral way of a booster consisting of a dose of vaccine corresponding to 0.5 mg/kg of *Listeria* antigen, mixed and partitioned in the daily diet.

Twenty animals were used for each posologic scheme. Sensitisation (primary treatment) was performed on the 30th day of life.

For the evaluation of the antibody response to vaccination, 15 days from the last booster dose, a blood sample was taken from the ear marginal vein of the animals. Antibody response was evaluated by the immunoenzymatic (ELISA) test with *Listeria* antigen (solubilised fraction) adhering to the microplate well and by detecting the immunoglobulins contained in the sample, bound by addition of a rabbit anti-immunoglobulin antibody conjugated with peroxidase, followed by addition of a specific chromogen for the enzyme.

The colour intensity was directly proportional to the amount of specific anti-*Listeria* IgGs contained in the antiserum.

Table 2 shows the mean O.D. values at different serum dilutions obtained, as per the two experimental protocols, with vaccine consisting of antigen conjugated with lectin and incorporated in chitosan or alginate.

TABLE 2

Anti-Listeria specific antibodies dosage following vaccination with Listeria antigen

| Group | Treatment | Mean O.D. at different serum dilutions | | |
|---|---|---|---|---|
| | | 1:5000 | 1:20000 | 1:80000 |
| A | Blank | 0.350 | | |
| B | Controls: no vaccination | 0.320 | 0.300 | 0.220 |
| C | Treated with vaccine in chitosan Posologic scheme (A) | 2.360 | 2.180 | 2.020 |
| D | Treated with vaccine in chitosan Posologic scheme (B) | 2.450 | 2.350 | 2.270 |
| E | Treated with vaccine in alginate Posologic scheme (A) | 2.220 | 2.200 | 2.120 |
| F | Treated with vaccine in alginate Posologic scheme (B) | 2.460 | 2.380 | 2.140 |

The data reported in Table 2 show that the vaccines prepared as per Example 1 (derivatised with lectins and incorporated in chitosan) induce antibodies production according to experimental immunisation protocol A as well as to experimental immunisation protocol B.

4.c. Evaluation of the Antibody Response to the Vaccination Against Polysaccharide-Complexed Infectious Rhinotracheitis (IRT) Antigen in the Chicken The vaccine consisting of IRT antigen conjugated with lectin and incorporated in chitosan or alginate was tested for the antibody response in the chicken. Chickens were administered the vaccine by the oral way, resuspended in drinking water, according to the following two posologic schemes:

Scheme A:
1. on day zero and on the next three days, administration of vaccine resuspended in drinking water at a dose corresponding to 0.5 mg/kg/die of IRT antigen;
2. on days 21 and 22, administration, according to the same procedure, of a dose corresponding to 0.2 mg/kg/die of IRT antigen.

Scheme B:
1. on day zero, subcutaneous injection of a quantity of vaccine corresponding to 0.3 mg/kg of IRT antigen (sensitisation reaction);
2. on days 7, 14 and 21, administration, by the oral way, of a booster resuspended in drinking water, corresponding to 0.2 mg/kg of IRT antigen, partitioned in daily watering.

For the evaluation of the antibody response to vaccination, 15 days from the last booster dose, a blood sample was taken from the animals.

Twenty chicks were used for each posologic scheme. Sensitisation (primary treatment) was performed on 7-day-old chicks.

Antibody response was evaluated by the immunoenzymatic (ELISA) test with IRT antigen (solubilised fraction) adhering to the microplate well and by detecting the imunoglobulins contained in the sample, bound by addition of a chicken anti-immunoglobulin antibody conjugated with peroxidase, followed by addition of a specific chromogen for the enzyme.

The colour intensity was directly proportional to the amount of specific anti-IRT IgGs contained in the antiserum.

Table 3 shows the mean O.D. values at different serum dilutions obtained, as per the experimental protocols, with vaccine consisting of antigen conjugated with lectin and incorporated in chitosan or alginate.

TABLE 3

Anti-IRT specific antibodies dosage following vaccination with IRT antigen

| Group | Treatment | Mean O.D. at different serum dilutions | | |
|---|---|---|---|---|
| | | 1:5000 | 1:20000 | 1:80000 |
| A | Blank | 0.250 | | |
| B | Controls: no vaccination | 0.360 | 0.260 | 0.100 |
| C | Treated with vaccine in chitosan Posologic scheme (A) | 1.720 | 1.540 | 1.305 |
| D | Treated with vaccine in chitosan Posologic scheme (B) | 1.840 | 1.760 | 1.580 |
| E | Treated with vaccine in alginate Posologic scheme (A) | 1.910 | 1.630 | 1.340 |
| F | Treated with vaccine in alginate Posologic scheme (B) | 1.840 | 1.620 | 1.530 |

The data reported in Table 3 show that the vaccines prepared as per Example 1 (derivatised with lectins and incorporated in chitosan) induce antibodies production according to experimental immunisation protocol A as well as to experimental immunisation protocol B.

4.d. Evaluation of the Antibody Response to the Vaccination Against the Polysaccharide-Complexed Respiratory Virus in the Chicken The vaccine consisting of the chicken respiratory virus antigen conjugated with lectin and incorporated in chitosan or alginate was tested for the antibody response. Chickens were administered the vaccine in drinking water, according to the following two posologic schemes:

Scheme A:
1. on day zero and the next three days, administration of vaccine resuspended in drinking water at a dose corresponding to 0.5 mg/kg/die of respiratory virus antigen, conjugated with lectin and incorporated in chitosan;
2. on days 21 and 22, administration, according to the same procedure, of a dose corresponding to 0.2 mg/kg/die of respiratory virus antigen.

Scheme B:
1. on day zero, subcutaneous injection of a quantity of vaccine corresponding to 0.3 mg/kg of respiratory virus antigen (sensitisation);

2. on days 7, 14 and 21, administration, by the oral way, of a booster, resuspended in drinking water, corresponding to 0.2 mg/kg of respiratory virus antigen, partitioned in daily watering.

For the evaluation of the antibody response to vaccination, 15 days from the last booster dose, a blood sample was taken from the animals.

Twenty chicks were used for each posologic scheme. Sensitisation (primary treatment) was performed on 7-day-old chicks.

Antibody response was evaluated by the immunoenzymatic (ELISA) test with the respiratory virus antigen (solubilised fraction) adhering to the microplate well and by detecting the immunoglobulins contained in the sample, bound by addition of a chicken anti-immunoglobulin antibody conjugated with peroxidase, followed by addition of a specific chromogen for the enzyme.

The colour intensity was directly proportional to the amount of specific anti-respiratory virus IgGs contained in the antiserum.

Table 4 shows the mean O.D. values at different serum dilutions obtained, as per the two experimental protocols, with vaccine consisting of antigen conjugated with lectin and incorporated in chitosan or alginate.

TABLE 4

Specific antibodies dosage following vaccination with respiratory virus antigen

| Group | Treatment | Mean O.D. at different serum dilutions | | |
|---|---|---|---|---|
| | | 1:5000 | 1:20000 | 1:80000 |
| A | Blank | 0.300 | | |
| B | Controls: no vaccination | 0.250 | 0.160 | 0.080 |
| C | Treated with vaccine in chitosan Posologic scheme (A) | 2.010 | 1.950 | 1.900 |
| D | Treated with vaccine in chitosan Posologic scheme (B) | 2.450 | 2.390 | 2.160 |
| E | Treated with vaccine in alginate Posologic scheme (A) | 1.980 | 1.900 | 1.820 |
| F | Treated with vaccine in alginate Posologic scheme (B) | 2.200 | 2.040 | 1.880 |

The data reported in Table 4 show that the vaccines prepared according to Example 1 (derivatised with lectins and incorporated in chitosan) induce antibodies production according to experimental immunisation protocol A as well as to experimental immunisation protocol B.

4.e. Evaluation of the Antibody Response to the Vaccination Against Polysaccharide-complexed *Candida albicans* Antigen in the Rat The vaccine consisting of *Candida albicans* antigen (prepared as per Example 1) conjugated with lectin and incorporated in chitosan or alginate was tested for the antibody response in the rat, by administering same, by means of a gastric probe, according to the following two posologic schemes:

Scheme A:
1. on day zero and the following day, administration of the incorporated vaccine by means of a gastric probe, (two administrations—sensitisation) at a dose of 0.3 mg/kg of antigen, in a suspension of 2% arabic gum;
2. on days 14 and 21, administration by the oral way and according to the same procedure, of a dose of incorporated vaccine corresponding to 0.2 mg/kg of antigen (candidin).

Scheme B:
1. on day zero, subcutaneous injection of a quantity of vaccine corresponding to 0.3 mg/kg of antigen (candidin);
2. on days 14 and 21, administration, by means of a gastric probe, of a booster consisting of a dose of incorporated vaccine corresponding to 0.1 mg/kg of antigen (candidin) per treatment, in a suspension of 2% arabic gum.

Scheme C:
the animals were vaccinated according to scheme A (sensitisation and boosters per os) by combining each administration with 1 mg/kg BVV incorporated in chitosan.

For the evaluation of the antibody response to vaccination, 15 days from the last booster dose, a blood sample was taken from the animals by intracardiac puncture.

Twenty adult male rats (200±10 g) were used for each posologic scheme.

Antibody response was evaluated by the immunoenzymatic (ELISA) test with candidin antigen adhering to the microplate well and by detecting the specific immunoglobulins contained in the sample, by addition of a rat anti-immunoglobulin antibody conjugated with peroxidase, followed by addition of a specific chromogen for the enzyme.

The colour intensity was directly proportional to the amount of specific anti-candidin IgGs contained in the sample.

Table 5 shows the mean O.D. values at different serum dilutions obtained, as per the three experimental protocols, with vaccine consisting of antigen conjugated with lectin and incorporated in chitosan or alginate, and in conjunction with BVV conjugates.

By way of comparison, a group was treated, according to the same procedure and dosages, with antigen non-conjugated with lectin, but incorporated with alginate.

TABLE 5

Anti-candidin specific antibodies dosage following vaccination with candidin antigen

| Group | Treatment | Mean O.D. at different serum dilutions | | |
|---|---|---|---|---|
| | | 1:5000 | 1:20000 | 1:80000 |
| A | Blank | 0.025 | | |
| B | Controls: no vaccination | 0.320 | 0.240 | 0.160 |
| C | Treated with vaccine in chitosan Posologic scheme (A) | 2.140 | 1.850 | 1.460 |
| D | Treated with vaccine in chitosan Posologic scheme (B) | 2.650 | 2.020 | 1.730 |
| E | Treated with vaccine in alginate Posologic scheme (A) | 2.000 | 1.810 | 1.520 |
| F | Treated with vaccine in alginate Posologic scheme (B) | 2.340 | 1.980 | 1.720 |
| G | Treated with vaccine in chitosan Posologic, in conjunction with BVV in chitosan scheme (C) | 2.980 | 2.950 | 2.560 |
| H | Treated with vaccine non-conjugated with lectin, incorporated in alginate Posologic scheme (A) | 1.050 | 0.680 | 0.290 |

The data reported in Table 5 show that the vaccines prepared as per Example 1 (derivatised with lectins and incorporated in chitosan) induce antibodies production according to experimental immunisation protocol A as well as to experimental immunisation protocol B. Furthermore, the above data show that the immunogenicity of candidin vaccine incorporated in alginate, but non-conjugated with lectin (group H) is lower than that of candidin derivatised with lectin.

Moreover as shown in the table the O.D. are higher in group G indicating that administration of BVV polysaccharides together with the vaccines of the invention enhances the specific immune response.

EXAMPLE 5

Immunisation with Vaccines Against Biologically Active Substances or Hormones. Analysis of the Vaccination Efficacy as Antibodies Production and/or Biological Activity In Vivo.

Vaccination efficacy against biologically active substances or hormones was evaluated in terms of antibody response and biological effect: for example, the vaccination against somatostatin may be used as a strategy to enhance body growth. In fact, anti-somatostatin antibodies neutralise the growth inhibitory effect of said hormone. It follows that the efficacy of said vaccination may be evaluated from the antibodies content and from the biological effect of growth enhancement, in comparison with non-vaccinated controls. According to the same criteria, the vaccination against calcitonin may be used as a strategy to improve calcium resorption from bones, the vaccination against glucagon to exogenically stimulate insulin endogenous release or to inhibit its release after administration (feedback effect), the vaccination against cholecystokinin may be used to exploit its role in satiety, the vaccination against cholesterol may be used for antiatherosclerotic purposes in man and to reduce, in the zootechnical field, the cholesterol content of products, such as milk, eggs, and meat.

5.a.1. Evaluation of the Antibody Response to the Vaccination with Somatostatin Antigen The vaccine efficacy to determine the specific antibody response in the adult rat (approx. 200 g) was tested. Groups of 20 animals each were treated according to the following posologic schemes:

Scheme A:
1. on day zero and for the next two days (three treatments in total), administration, by means of a gastric probe, of a dose of vaccine corresponding to 0.3 mg/kg of antigen (inactivated somatostatin), in a suspension of 2% arabic gum;
2. on days 14 and 21, administration, by means of a gastric probe and according to the same procedure, of a booster consisting of a dose of vaccine corresponding to 0.2 mg/kg/dose of antigen.

Scheme B:
1. on day zero, subcutaneous injection of a quantity of vaccine corresponding to 0.1 mg/kg of antigen;
2. on days 14 and 21, administration, by means of a gastric probe, of a booster consisting of a dose of incorporated vaccine corresponding to 0.3 mg/kg/dose of antigen, in a suspension of 2% arabic gum.

For the evaluation of the antibody response to vaccination, 15 days from the last booster dose, a blood sample was taken from the animals by intracardiac puncture.

Antibody response was evaluated by the immunoenzymatic (ELISA) test with a protein-somatostatin (BSA-somatostatin) conjugate adhering to the microplate well and by detecting the specific antistomatostatin immunoglobulins contained in the serum, by addition of a rat anti-immunoglobulin antibody conjugated with peroxidase, followed by addition of a specific chromogen for the enzyme.

The colour intensity was directly proportional to the amount of specific anti-somatostatin IgGs contained in the sample and, therefore, induced by vaccination. Table 6 shows the mean O.D. values at different serum dilutions obtained as per the two experimental protocols.

TABLE 6

Anti-somatostatin specific antibodies dosage following vaccination with the claimed conjugates, according to protocols A and B

| Group | Treatment | Mean O.D. at different serum dilutions | | |
|---|---|---|---|---|
| | | 1:5000 | 1:20000 | 1:80000 |
| A | Blank | 0.040 | | |
| B | Controls: no vaccination | 0.250 | 0.220 | 0.180 |
| C | Treated with vaccine in chitosan Posologic scheme (A) | 0.980 | 0.740 | 0.630 |
| D | Treated with vaccine in chitosan Posologic scheme (B) | 1.140 | 0.920 | 0.770 |
| E | Treated with vaccine in alginate Posologic scheme (A) | 0.920 | 0.740 | 0.640 |
| F | Treated with vaccine in alginate Posologic scheme (B) | 1.060 | 0.940 | 0.780 |

The data reported in Table 6 show that the vaccines prepared as per Example 1 (derivatised with lectins and incorporated in chitosan) induce antibodies production according to experimental immunisation protocol A as well as to experimental immunisation protocol B.

5.a.2. Evaluation of the Biological Effect of the Vaccination with Somatostatin Antigen on Body Growth The influence of active anti-somatostatin vaccination on the body growth rate and extent was evaluated on rats (80 g), subdivided into groups of 10 animals.

The groups were subjected to the following treatments:

Group 1: controls, no vaccination.

Group 2: treated with anti-somatostatin vaccine according to the following experimental protocol (posologic scheme A):
  on day zero, administration, by means of a gastric probe, of a dose of vaccine incorporated in chitosan, corresponding to 0.8 mg/kg of inactivated somatostatin antigen, suspended in 1 ml of 2% arabic gum;
  on days 14 and 21, administration, by means of a gastric probe, of a booster consisting of a dose of vaccine incorporated in chitosan, corresponding to 0.1 mg/kg of inactivated somatostatin antigen, in 1 ml of 2% arabic gum.

Group 3: treated with anti-somatostatin vaccine according to the following experimental protocol (posologic scheme B):
  Sensitisation with anti-somatostatin vaccine incorporated in chitosan, administered by the subcutaneous parenteral way at a dose corresponding to 0.1 mg/kg of inactivated somatostatin antigen.
  On days 14 and 21, administration, by means of a gastric probe, of a booster consisting of a dose of anti-somatostatin vaccine corresponding to 0.3 mg/kg of inactivated somatostatin antigen, on day 0, in 1 ml of in 2% arabic gum.

Group 4: treated according to the same posologic scheme as adopted for Group 2 (posologic scheme A), but with vaccine incorporated in alginate.

Group 5: treated according to the same posologic scheme as adopted for Group 3 (posologic scheme B), but with vaccine incorporated in alginate.

During the whole test, animals had free access to food and drinking water, the latter being added with L-arginine and DL-aspartic acid. In this way, rats received a daily dose of 25 mg/kg of each amino acid (amino acids were administered as exogenous activators of the somatotropic hormone).

The body weight of each rat was controlled at the test start and every 7 days; the rats general state was controlled daily.

Table 7 shows the average percent bodyweight variations with time of groups vaccinated against somatostatin in comparison with controls.

TABLE 7

Evaluation of the anti-somatostatin vaccination biological efficacy

| | | average % bodyweight on days: | | | | |
|---|---|---|---|---|---|---|
| Group | Treatment | 7 | 14 | 21 | 28 | 35 |
| A | Controls-no treatment | — | — | — | — | — |
| B | Treated with anti-somatostatin vaccine in chitosan (scheme A) | +2.5 | +5.7 | +10.1 | +14.3 | +21.5 |
| C | Treated with anti-somatostatin vaccine in chitosan (scheme B) | +3.7 | +6.2 | +13.4 | +18.5 | +28.7 |
| D | Treated with anti-somatostatin vaccine in alginate (scheme A) | +2.0 | +4.0 | +8.7 | +14.0 | +23.0 |
| E | Treated with anti-somatostatin vaccine in alginate (scheme B) | +3.9 | +4.5 | +9.0 | +16.7 | +27.4 |

The data shown in Table 7 demonstrate that the active vaccination against somatostatin allows the activation, by the oral way, of the somatotropic hormone due to the neutralisation of the inhibitor endogenous portion produced by feedback. Consequently, in comparison with non-vaccinated controls, the growth is substantially and significantly enhanced.

5.b. Evaluation of the Response to the Vaccination Against Calcitonin Antigen Activated with Lectin and Incorporated in Chitosan or Alginate. Evaluation of the Antibody Response The vaccine efficacy to determine the specific response in the adult rat (200 g) was tested. Groups of 20 animals each were treated according to the following posologic schemes:

Group C, Scheme A: the anti-calcitonin vaccine in chitosan was administered according to the same procedure and dosages as per scheme A of the previous example.
Group D, Scheme B: the anti-calcitonin vaccine in chitosan was administered according to the same procedure and dosages as per scheme B of the previous example.
Group E, Scheme A: the anti-calcitonin vaccine in alginate was administered according to the same procedure and dosages as per scheme A of the previous example.
Group F, Scheme B: the anti-calcitonin vaccine in alginate was administered according to the same procedure and dosages as per scheme B of the previous example.

A further group (B) was used as a control and did not receive any treatment.

For the evaluation of the antibody response to vaccination, 15 days from the last booster dose, a blood sample was taken from the animals by intracardiac puncture.

Antibody response was evaluated by the immunoenzymatic (ELISA) test with a protein-calcitonin (calcitonin-KLH) conjugate—prepared as per the schemes set forth for the conjugation with lectin—adhering to the microplate well and by detecting the specific anti-calcitonin immunoglobulins contained in the serum (sample) by addition of a rat anti-immunoglobulin antibody conjugated with peroxidase, followed by addition of a specific chromogen for the enzyme.

The colour intensity was directly proportional to the amount of specific anti-calcitonin IgGs contained in the sample.

Table 8 shows the mean O.D. values at different serum dilutions obtained as per the two experimental protocols.

TABLE 8

Specific antibodies dosage in animals vaccinated against calcitonin antigen

| | | Mean O.D. at different serum dilutions | | |
|---|---|---|---|---|
| Group | Treatment | 1:5000 | 1:20000 | 1:80000 |
| A | Blank | 0.300 | | |
| B | Controls. no vaccination | 0.220 | 0.180 | 0.120 |
| C | Treated with vaccine in chitosan Posologic scheme (A) | 0.800 | 0.680 | 0.490 |
| D | Treated with vaccine in chitosan Posologic scheme (B) | 1.070 | 0.920 | 0.800 |
| E | Treated with vaccine in alginate Posologic scheme (A) | 0.900 | 0.740 | 0.600 |
| F | Treated with vaccine in alginate Posologic scheme (B) | 1.020 | 0.940 | 0.820 |

The data reported in Table 8 show that the vaccines prepared as per Example 1 (derivatised with lectins and incorporated in chitosan) induce antibodies production according to experimental immunisation protocol A as well as to experimental immunisation protocol B.

5.c. Evaluation of Vaccination Effects Against the Glucagon Antigen Derivatised with Lectin and Incorporated in Chitosan or Alginate. Evaluation of the Antibody Response The vaccine efficacy to determine the specific antibody response in the adult rat (approx. 200 g) was tested. Groups of 20 animals each were treated according to the following posologic schemes:

Group B: controls: no vaccination.
Group C: animals subjected to anti-glucangon vaccination treatments according to posologic scheme A) envisaging:
1. on day zero and on the next day administration, by means of a gastric probe, of the vaccine incorporated in chitosan at a dose of 0.3 mg/kg of antigen (sensitisation), in a 2% suspension of arabic gum;
2. on days 14 and 21, administration, by the oral way, according to the same procedure, of a booster consisting of a vaccine incorporated in chitosan, corresponding to 0.2 mg/kg of antigen (inactivated glucagon—boosters).

Group D: animals subjected to antiglucagon vaccination according to the posologic scheme B) envisaging:
1. on day zero, subcutaneous injection of a quantity of anti-glucagon vaccine incorporated in chitosan, corresponding 0.1 mg/kg of antigen (inactivated glucagon—sensitisation);
2. on days 14 and 21, administration, by means of a gastric probe, of a booster consisting of a dose of anti-glucagon vaccine incorporated in chitosan, corresponding to 0.3 mg/kg/dose of antigen (inactivated glucagon—boosters), in a suspension of 2% arabic gum.

Group E: animals subjected to anti-glucagon vaccination with vaccine incorporated in alginate according to the posologic scheme A).
Group F: animals subjected to anti-glucagon vaccination with vaccine incorporated in alginate according to the posologic scheme B).

For the evaluation of the antibody response to vaccination, 15 days from the last booster dose, a blood sample was taken from the animals by intracardiac puncture and centrifuged (3000 rpm, 15 min) for serum collection.

Antibody response was evaluated by the immunoenzymatic (ELISA) test with the antigen (glucagon—KLH prepared according to the aforementioned conjugation scheme and in the absence of lectin) adhering to the microplate well and by detecting the specific anti-glucagon immunoglobulins contained in the sample, by addition of a rat anti-immunoglobulins antibody conjugated with peroxidase, followed by addition of a specific chromogen for the enzyme.

The microplate (glucagon antigen-KLH adhesion) was prepared by adding each well with an antigen solution (125 µl/well) at a concentration of 10 pg/mL in a 0.1 M carbonate buffer, pH 9.5, and leaving it in contact with the well for 3 hrs in a thermostat at 37° C.

Once repeated washings for the removal of non-adhering antigen excess were carried out, the well surface was saturated by adding each well with 200 µl/well of a 2% casein solution in 0.05 M phosphate-saline buffer (PBS), pH 7.4; saturation was carried out for 2 hrs in a thermostat at 37° C. for casein removal, by three washings.

The antiserum (sample) to be examined was diluted at different levels with 0.1 M phosphate-saline buffer (PBS), pH 7.4. The different serum dilutions (100 µL) were added to the wells and maintained in contact therewith for 1 hr at 37° C. The non-adhering material was removed by washing with a wash solution consisting of 0.01 M PBS, pH 7.4, containing 0.1% Tween 20.

For the detection, each well was added with rat anti-lgG conjugate (100 µL/well). HRP (Sigma A9542) was diluted to the concentrations indicated by the manufacturer with 0.1 M PBS, pH 7.4, containing 0.1% (p/r) casein. The anti IgG HRP conjugate was maintained in contact with the well for 1 hr at 37° C.

Once three washings with the aforementioned wash solution were performed, 100 µL OPD (urea peroxide) (Sigma P6662), prepared according to the manufacturer's directions in a 0.1 M citrate/phosphate buffer, pH 5.5, was added to each well and incubated for 30 min in a thermostat at 37° C.

The reaction was discontinued by adding each well with 1 M H2SO4 (50 µL). Readings were performed at 490 nm.

The colour intensity was directly proportional to the amount of specific anti-glucagon IgGs contained in the sample (serum).

Table 9 shows the mean O.D. values at different serum dilutions obtained, as per the two experimental protocols, with anti-glucagon vaccine prepared by conjugation with lectin, followed by conjugate incorporation in chitosan or alginate.

TABLE 9

Specific antibodies dosage following vaccination with anti-glucagon vaccine

| | | Mean O.D. at different serum dilutions | | |
|---|---|---|---|---|
| Group | Treatment | 1:5000 | 1:20000 | 1:40000 |
| A | Blank | 0.024 | | |
| B | Controls: no vaccination | 0.160 | 0.120 | 0.050 |
| C | Treated with anti-glucagon vaccine in chitosan Posologic scheme (A) | 0.800 | 0.920 | 0.750 |
| D | Treated with anti-glucagon vaccine in chitosan Posologic scheme (B) | 1.040 | 0.940 | 0.720 |
| E | Treated with anti-glucagon vaccine in alginate Posologic scheme (A) | 1.160 | 0.750 | 0.570 |
| F | Treated with anti-glucagon vaccine in alginate Posologic scheme (B) | 1.020 | 0.860 | 0.640 |

The data reported in Table 9 show that the antigens according to the invention (derivatised with lectins and incorporated inpolysaccharides) induce antibodies production according to experimental immunisation protocol A as well as to experimental immunisation protocol B.

5.d. Evaluation of the Vaccination Effects Against Cholecystokinin Antigen Derivatised with Lectin and Incorporated in Chitosan and Alginate. Evaluation of the Antibody Response The vaccine efficacy to determine the specific antibody response in the adult rat (approx. 200 g) was tested. Groups of 20 animals each were treated according to the following posologic schemes:

Group B, controls: no vaccination

Group C: animals subjected to anti-cholecystokinin vaccination with vaccine incorporated in chitosan according to the posologic scheme A (as per scheme A of the vaccination with anti-glucagon vaccine, point 5c);

Group D: animals subjected to anti-cholecystokinin vaccination with vaccine incorporated in chitosan according to posologic scheme A (as per scheme B of the vaccination with anti-glucagon vaccine, point 5c);

Group E: animals subjected to anti-cholecystokinin vaccination with vaccine incorporation in chitosan according to posologic scheme A;

Group F: animals subjected to anti-cholecystokinin vaccination with vaccine incorporated in alginate according to posologic scheme B;

Group G: animals subjected to anti-cholecystokinin vaccination with vaccine non-conjugated with lectin, but incorporated in chitosan (posologic scheme A).

For the evaluation of the antibody response to vaccination, 15 days from the last booster dose, a blood sample was taken from the animals and treated as per the above Examples for serum collection.

Antibody response was evaluated by the ELISA test as per the procedure described in Example 4), using microplates with cholecystokinin-KLH antigen, adhering thereto, obtained according to the synthesis scheme already described, without lectin addition.

The methods for microplates, coniugate, chromogen/substrate and sample preparation as well as for test performance and readings were as described for anti-glucagon vaccination.

Colour intensity was directly proportional to the amount of specific anti-cholecystokinin IgGs contained in the sample (serum).

Table 10 shows the mean O.D. values at different serum dilutions obtained, as per the two experimental protocols, with anti-cholecystokinin vaccine, prepared by conjugation with lectin, followed by conjugate incorporation in chitosan or alginate.

TABLE 10

Specific antibodies dosage following anti-cholecystokinin vaccination

| | | Mean D.O. at different serum dilutions | | |
|---|---|---|---|---|
| Group | Treatment | 1:5000 | 1:20000 | 1:40000 |
| A | Blank | 0.040 | | |
| B | Controls: no vaccination | 0.283 | 0.200 | 0.140 |
| C | Anti-cholecystokinin vaccine in chitosan Scheme (A) | 1.140 | 0.980 | 0.750 |
| D | Anti-cholecystokinin vaccine in chitosan Scheme (B) | 1.250 | 1.020 | 0.860 |
| E | Anti-cholecystokinin vaccine in alginate Scheme (A) | 1.090 | 0.950 | 0.800 |

TABLE 10-continued

Specific antibodies dosage following anti-cholecystokinin vaccination

| Group | Treatment | Mean D.O. at different serum dilutions | | |
|---|---|---|---|---|
| | | 1:5000 | 1:20000 | 1:40000 |
| F | Anti-cholecystokinin vaccine in alginate Scheme (B) | 1.160 | 1.000 | 0.880 |
| G | Anti-cholecystokinin vaccine not derivatised but incorporated in chitosan (Scheme A) | 0.820 | 0.740 | 0.205 |

The data reported in Table 10 show that the antigens (derivatised with lectins and incorporated in chitosan) induce antibodies production according to experimental immunisation protocol A as well as to experimental immunisation protocol B. Furthermore, said data show that the immunogenicity of the anti-cholecystokinin vaccine incorporated in alginate, but not conjugated with lectin (Group G), is clearly lower than that of candidin derivatised with lectin.

5.e. Evaluation of the Vaccination Effects Against Cholesterol Antigen Derivatised with Lectin and Incorporated in Chitosan or Alginate.

5.e.1. Evaluation of the Antibody Response

The vaccine efficacy to determine the specific antibody response in the adult rat (approx. 200 g) was tested. Groups of 20 animals each were treated according to the following posologic schemes:

Group B, controls: no vaccination

Group C: animals treated with anti-cholesterol vaccine. The vaccine incorporated in chitosan was administered according to the same procedure and dosages as per posologic scheme A (scheme A of the anti-glucagon vaccination, point 5c);

Group D: animals treated with anti-cholesterol vaccine. The vaccine was administered according to the same procedure and dosages as per posologic scheme B (scheme B of the anti-glucagon vaccination, point 5c);

Group E: animals treated with anti-cholesterol vaccine. The vaccine was administered according to the same procedure and dosages as per posologic scheme B (scheme B of the anti-glucagon vaccination, point 5c);

Group F: animals treated with anti-cholesterol vaccine. The vaccine was administered according to the same procedure and dosages as per posologic scheme B (scheme B of the anti-glucagon vaccination, point 5c);

Group G: animals treated with anti-cholesterol vaccine incorporated in chitosan, according to posologic scheme A, in conjunction with BVV in chitosan, as an adjuvant, at the dose of 1 mg/kg/dose.

For the evaluation of the antibody response, 15 days from the last booster dose, a blood sample was taken from the animals and treated as per the above Examples for serum collection.

Antibody response was evaluated by the ELISA test as per the procedure described under point 5.c.), using microplates with cholesterol-KLH antigen adhering thereto, which was obtained according to the synthesis scheme already described.

The methods for microplates, conjugate, chromogen/substrate and sample preparation as well as for test performance and reading of the results were as described for anti-glucagon vaccination.

Table 11 shows the mean O.D. values at different serum dilutions obtained, as per the two experimental protocols, with anti-cholesterol vaccine, prepared by conjugation with lectin, followed by conjugate incorporation in chitosan or alginate.

TABLE 11

Specific antibodies dosage following anti-cholesterol vaccination

| Group | Treatment | Mean O.D. at different serum dilutions | | |
|---|---|---|---|---|
| | | 1:5000 | 1:20000 | 1:40000 |
| A | Blank | 0.030 | | |
| B | Controls: no vaccination | 0.260 | 0.160 | 0.080 |
| C | Treated with anti-cholesterol vaccine in chitosan Scheme (A) | 1.060 | 0.840 | 0.620 |
| D | Treated with anti-cholesterol vaccine in chitosan Scheme (B) | 1.120 | 0.900 | 0.740 |
| E | Anti-cholesterol vaccine in alginate Scheme (A) | 0.980 | 0.820 | 0.720 |
| F | Anti-cholesterol vaccine in alginate Scheme (B) | 1.020 | 0.940 | 0.860 |
| G | Anti-cholesterol vaccine in chitosan Scheme (A) | 2.040 | 1.860 | 1.420 |

The data reported in Table 11 show that the cholersterol antigen (derivatised with lectins and incorporated inpolysaccharides) induce antibodies production according to experimental immunisation protocol A as well as to experimental immunisation protocol B.

5.e.2. Evaluation of the Biological Effects of Anti-Cholesterol Vaccine According to the Invention Experiments were carried out on male Wistar rats, 100±10 g, subdivided into groups of 10 units/each, which were subjected to the following treatments:

Group 1, controls: no vaccination. Rats were fed for the whole test period with a standard diet for rats;

Group 2: hypercholesteremia control: no vaccination. Rats were fed from day 1 to day 30 with a standard diet for rats, and from day 31 with cholesterol-rich hyperlipidic diet (10% of the fat composition);

Group 3: rats were vaccinated with anti-cholesterol vaccine in chitosan according to posologic scheme A), (scheme A of the anti-glucagon vaccination, point 5c) envisaging the sensitisation dose per os at time zero, followed by booster administration per os on days 14 and 21.

Rats were fed from time zero to day 30 with the standard diet for rats and from day 31 with cholesterol-rich hyperlipidic diet (30% of the fat composition).

Group 4: rats were vaccinated with anti-cholesterol vaccine in chitosan according to posologic scheme B) (scheme B of the anti-glucagon vaccination, point 5c) envisaging the sensitisation dose by the parenteral way at time zero and boosters by the oral way on days 14 and 21.

Rats were fed from time 0 to day 30 with the standard diet for rats and from day 31 with a cholesterol-rich hyperlipidic diet (30% of the fat composition)

Group 5: rats were vaccinated with anti-cholesterol vaccine in chitosan according to posologic scheme B) envisaging the sensitisation dose by the parenteral way at time 0 and boosters by the oral way on days 14 and 21 (same scheme as for Group 4).

Rats were fed, from time 0, with cholesterol-rich hyperlipidic diet (30% of the fat composition).

This experiment was not conducted on the corresponding vaccine incorporated in alginate, the antibody responses to vaccination found in the analysis of the two incorporation forms being superimposable.

On days 45, 60 and 90 from time zero (on days 15, 30 and 60 from the fat diet start for groups 2, 3 and 4), a blood sample was taken from animals by intracardiac punture, which was centrifuged (3000 rpm, 15 min) for the separation of the serum meant for the determination of cholesterol levels.

Said determination was carried out by the colourimetric enzymatic method (Kit Sigma cod. 352–80).

Table 12 shows the percent variations in serum total cholesterol concentrations evaluated in comparison with controls fed with a standard diet (the latter concentrations being considered equal to 100).

TABLE 12

Evaluation of the biological effect of anti-cholesterol vaccination

| Group | Treatment | Δ% cholesterol concentration on days: | | |
|---|---|---|---|---|
| | | 45 | 60 | 90 |
| 1 | No vaccination Standard diet | — | — | — |
| 2 | No vaccination Hyperlipidic diet from day 31 | +9.4 | +17.5 | +18.9 |
| 3 | Vaccinated, scheme A) Hyperlipidic diet from day 31 | −14.2 | −15.7 | −12.2 |
| 4 | Vaccinated, scheme B) Hyperlipidic diet from day 31 | −17.5 | −18.4 | −14.6 |
| 5 | Vaccinated, scheme B) Hyperlipidic diet from time 0 | −8.7 | −10.2 | −7.6 |

The data of Table 12 show the biological efficacy of anti-cholesterol vaccination in lipid accumulation in the rat fed with hyperlipemic diet; in particular, it shows that the active vaccination against cholesterol can maintain, below norm, the lipid levels in the blood of animals fed with hypercholesteremic fat diet.

The vaccination effect is clear also in animals with hypercholesteremia induced before vaccination.

5.f. Evaluation of the Vaccination Effects Against Cocaine Antigen Derivatised with Lectin and Incorporated in Chitosan or Alginate.

5.f.1. Evaluation of the Antibody Response

The vaccine efficacy to determine the antibody response in the adult rat (approx. 200 g) was tested. Groups of 20 animals each were treated according to the following posologic schemes:

Group B, controls: no vaccination
Group C: animals treated with anti-cocaine vaccine incorporated in chitosan according to posologic scheme A (scheme A of the anti-glucagon vaccination, point 5c);
Group D: animals treated with anti-cocaine vaccine incorporated in chitosan according to scheme B (scheme B of the anti-glucagon vaccination, point 5c);
Group E: animals subjected to the same treatment as Group C), but with vaccine incorporated in alginate;
Group F: animals subjected to the same treatment as Group B), but with vaccine incorporated in alginate;

A blood sample was taken from the animals for serum collection, 15 days from the last booster, according to the same procedure as described above.

Antibody response was evaluated by the ELISA test, carried out as described above and with microplate wells filled with the cocaine antigen, prepared as described by O. Bagasra (Immunopharmachology, 1992, 23, 173).

Table 13 shows the mean O.D. values at different serum dilutions obtained, as per the two experimental protocols, with anti-cocaine vaccine, prepared by conjugation with lectin, followed by conjugate incorporation in chitosan or alginate.

TABLE 13

Specific antibodies dosage following anti-cocaine vaccination

| | | Mean O.D. at different serum dilutions | | |
|---|---|---|---|---|
| Group | Treatment | 1:5000 | 1:20000 | 1:40000 |
| A | Blank | 0.030 | — | — |
| B | Controls: no vaccination | 0.280 | 0.200 | 0.140 |
| C | Treated with anti-cocaine vaccine in chitosan. Posologic scheme A) | 1.380 | 1.160 | 0.940 |
| D | Treated with anti-cocaine vaccine in chitosan. Posologic scheme B) | 1.450 | 1.280 | 1.140 |
| E | Treated with anti-cocaine vaccine in alginate. Posologic scheme A) | 1.420 | 1.300 | 1.150 |
| F | Treated with anti-cocaine vaccine in alginate. Posologic scheme B) | 1.156 | 1.340 | 1.090 |

The data reported in Table 13 show that the cocaine antigen (derivatised with lectins and incorporated in chitosan) induce antibodies production according to experimental immunisation protocol A as well as to experimental immunisation protocol B.

5.f.2. Evaluation of the Biological Effects of Anti-Cocaine Vaccine

The anaesthetic response in the rat was assayed by the hot-plate test according to O. Bagasra et al. (Immunopharmacology 1992, 23,173).

Male Swiss mice (20 g) were subdivided into groups of 20 mice each and were treated as follows:
Group 1: controls, no treatment;
Group 2: animals subjected to vaccination with derivatised anti-cocaine vaccine incorporated in chitosan according to posologic scheme A (scheme A of the anti-glucagon vaccination, point 5c);
Group 3: animals subjected to vaccination with anti-cocaine vaccine incorporated in chitosan according to scheme B (scheme B of the anti-glucagon vaccination, point 5c);
Group 4: animals subjected to the same treatment as that of Group 2), but with vaccine incorporated in alginate;
Group 5: animals subjected to the same treatment as that of Group 3), but with vaccine incorporated in alginate;

On day 36 from time zero (primary vaccine administration—sensitisation), i.e. 15 days from the last booster, animals were administered 25 mg/kg cocaine in a physiological solution, by the intraperitoneal way.

After one hour, mice were placed on a plate thermostatically set at 55° C. and the animal reaction time (sec) to thermal stimulation was controlled.

Table 14 shows the percent response variations in comparison with controls administered cocaine only.

TABLE 14

Evaluation of the biological effect of anti-cocaine vaccination

| Group | Treatment | Reduction (%) in response times to thermal stimulation |
|---|---|---|
| 1 | Controls: no pretreatment | — |
| 2 | Pretreated with anti-cocaine vaccine in chitosan. Scheme A) | 48.0 |
| 3 | Pretreated with anti-cocaine vaccine in chitosan. Scheme B) | 60.0 |

TABLE 14-continued

Evaluation of the biological effect of anti-cocaine vaccination

| Group | Treatment | Reduction (%) in response times to thermal stimulation |
|---|---|---|
| 4 | Pretreated with anti-cocaine vaccine in alginate. Scheme A) | 46.0 |
| 5 | Pretreated with anti-cocaine vaccine in alginate. Scheme B) | 60.0 |

The results recapitulated in Table 14 show that active vaccination against cocaine can significantly antagonise its anaesthetic effects, thanks to the production of specific anti-cocaine antibodies, which antagonise its pharmacological activity.

5.g. Vaccine Efficacy Against *Poa Pratensis* Allergies

Assays were performed on adult human volunteers who, from diagnostic tests, showed an evident allergy to *Poa pratensis* with a consequent documented occurrence of recurrent clinical episodes (rhinitis).

Subjects were subdivided at random into groups of 10 and were subjected to the following treatments:

Group 1: controls, no treatment;

Groups 2: treated per os with anti-*Poa pratensis* vaccine conjugated with lectin and incorporated in chitosan, at a concentration of 2 mg vaccine/dose according to the following posologic scheme: No. 7 administrations, one every 5 days, in the January–February period+No. 7 administrations, one every 5 days, in the August–September period.

Group 3: treated as Group 2, but with the vaccine dose combined with 0.5 mg BVV immunomodulator incorporated in chitosan.

From the vaccination start and for the next 18 months, the frequency of allergic clinical episodes was checked on the basis of data reported by the same subjects on proper forms.

Table 15 shows the percent reduction in clinical episodes of vaccinated subjects in comparison with the episodes occurring in controls (the latter being considered equal to 100).

TABLE 15

Biological effect of the vaccination with anti-poa antigens in chitosan and in conjunction with BVV immunostimulant

| Group | Treatment | % reduction of allergic episodes in comparison with controls |
|---|---|---|
| 1 | Controls, no treatment | — |
| 2 | Treated per os with anti-poa vaccine in chitosan | 80 |
| 3 | Treated per os with anti-poa vaccine + BVV in chitosan | 100 |

The data of Table 15 show that the immunisation with derivatised *Poa pratensis* antigen incorporated in chitosan significantly reduces the number of clinical episodes in treated subjects in comparison with controls.

What is claimed is:

1. An immunogenic composition comprising as an active ingredient an antigen selected from the group consisting of:

vaccines, microorganisms, infectious agents, and microorganism and infectious agents soluble or unsoluble fractions wherein said antigen is covalently conjugated to a lectin, further comprising a polysaccharidic coating.

2. The immunogenic composition according to claim 1, wherein said polysaccharidic coating is selected from the group consisting of: chitosan, methylglycolchitosan, alginic acid, polymannuronic acid and salts thereof.

3. The immunogenic composition according to claim 1, wherein the polysaccharidic coating is linked by non-covalent bonds to the lectin conjugate antigen.

4. The immunogenic composition according to claim 3, wherein said non-covalent bonds are ionic bonds.

5. Composition according to claim 1, wherein said infectious agents are selected from the group consisting of: Herpes simplex virus, Cytomegalovirus (CMV), Chicken pox virus, Rubella virus, syncytial virus, respiratory virus, influenza virus, Epstein-Barr virus, *Listeria monocytogenes*, *Salmonella enteritidis*, *Salmonella typhi*, *Salmonella paratyphi*, *Salmonella typhimurium*, *Salmonella choleraensis*, *Clostridium tetani*, *Clostridium botulinum*, *Shigella flexneri*, *Candida albicans*, *Toxoplasma gondii*.

6. Composition according to claim 5, wherein the infectious agent is *Candida albicans* or antigenic constituents thereof.

7. Composition according to claim 5 wherein the infectious agent is *Listeria monocytogenes*.

8. Composition according to claim 5 wherein the infectious agent is the chicken respiratory virus.

9. Composition according to claim 1, wherein said lectins are proteins of vegetable origin.

10. Composition according to claim 9, wherein said lectins are selected from the group consisting of *Lens culinaris* lectin, *Glycine max* lectin, *Ulex Europaeus* (UEAI+UEAII) lectin, *Arachis hypogaea* lectin, *Phaseolus vulgaris* lectin, soybean lectin.

11. Composition according to claim 1, wherein said lectins are covalently conjugated to the antigen by reaction between the aldehydic and aminate groups.

12. Composition according to claim 1 for oral and transmucosal administration.

13. Composition according to claim 12, wherein said transmucosal administration is buccal, perlingual, rectal, vaginal or nasal.

14. Compositions according to claim 1 wherein the active ingredient is in combination with suitable adjuvants and/or excipients.

15. Compositions according to claim 14 for oral and/or transmucosal administration.

16. The compositions according to claim 14, wherein said adjuvant is a delipidated *Corynebacterium granulosum* (BVV) fraction incorporated in polysaccharides.

* * * * *